(12) United States Patent
Port

(10) Patent No.: US 9,833,521 B2
(45) Date of Patent: *Dec. 5, 2017

(54) METHOD FOR PREPARING A PHARMACEUTICAL FORMULATION OF LANTHANIDE CHELATE IN POWDER FORM

(71) Applicant: GUERBET, Villepinte (FR)

(72) Inventor: Marc Port, Deuil la Barre (FR)

(73) Assignee: GUERBET, Villepinte (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/147,570

(22) Filed: May 5, 2016

(65) Prior Publication Data

US 2016/0243265 A1    Aug. 25, 2016

Related U.S. Application Data

(63) Continuation of application No. 13/319,901, filed as application No. PCT/EP2010/056603 on May 12, 2010, now Pat. No. 9,352,056.

(30) Foreign Application Priority Data

May 13, 2009    (FR) ..................... 09 53147

(51) Int. Cl.
*A61K 49/10* (2006.01)
*A61K 49/06* (2006.01)
*A61K 9/08* (2006.01)

(52) U.S. Cl.
CPC ............. *A61K 49/108* (2013.01); *A61K 9/08* (2013.01); *A61K 49/06* (2013.01)

(58) Field of Classification Search
CPC ......... A61K 49/108; A61K 49/06; A61K 9/08
USPC ....................................... 424/1.11
See application file for complete search history.

(56) References Cited

U.S. PATENT DOCUMENTS

| 4,647,447 A | 3/1987 | Gries et al. |
| 5,148,833 A | 9/1992 | Ota |
| 5,648,063 A | 7/1997 | Gries et al. |
| 5,650,133 A | 7/1997 | Carvalho et al. |
| 5,876,695 A | 3/1999 | Gries et al. |
| 9,352,056 B2 * | 5/2016 | Port et al. ............. 424/1.11 |
| 2004/0170566 A1 | 9/2004 | Chang et al. |
| 2009/0208421 A1 | 8/2009 | Meyer et al. |
| 2011/0129425 A1 | 6/2011 | Meyer et al. |

FOREIGN PATENT DOCUMENTS

| CA | 1256249 A | 6/1989 |
| EP | 0270483 A2 | 6/1988 |
| EP | 0481526 A1 | 4/1990 |
| EP | 0450078 A1 | 10/1991 |
| FR | 2590484 A1 | 5/1987 |
| FR | 2927539 A1 | 8/2009 |
| WO | WO 2009/103744 A2 | 8/2009 |

OTHER PUBLICATIONS

Corot et al., "Structure-Activity Relationship of Macrocylic and Linear Gadolinium Chelates: Investigation of Transmetallation Effect on the Zinc-Dependent Metallopeptodase Angiotensin-Converting Enzyme," JMRI, vol. 8, No. 3, May/Jun. 1998, pp. 695-702, XP00809734.
Idee et al., "Clinical and Biological Consequences of Transmetallation Induced by Contrast Agents for Magnetic Resonance Imaging: A Review," Fundamental & Clinical Pharmacology, vol. 20, 2006, pp. 563-576, XP002549063.
Notification of Transmittal of the International Search Report and the Written Opinion of the International Searching Authority and International Search Report dated Oct. 18, 2010 for International Application No. PCT/EP2010/056603 (Forms PCT/ISA/220, PCT/ISA/210 and PCT/ISA/237).
Grobner et al., Kidney International, vol. 72, 2007, pp. 260-264.
Hagan et al., Anal. Chem., vol. 60, pp. 514-516, 1988.
Williamson, Macroscale and Microscale Organic Experiments, pp. 39-42, 1994.

* cited by examiner

*Primary Examiner* — Michael G Hartley
*Assistant Examiner* — Sean Donohue
(74) *Attorney, Agent, or Firm* — Birch, Stewart, Kolasch & Birch, LLP

(57) ABSTRACT

The present invention relates to a method for preparing a pharmaceutical formulation of lanthanide chelate in powder form, wherein the powder constitutes a mol/mol excess of free chelate of between 0.002 and 0.4%.

13 Claims, No Drawings

METHOD FOR PREPARING A PHARMACEUTICAL FORMULATION OF LANTHANIDE CHELATE IN POWDER FORM

This application is a continuation of U.S. patent application Ser. No. 13/319,901 filed on Dec. 21, 2011, now U.S. Pat. No. 9,352,056, which is the national phase of PCT International Application No. PCT/EP2010/056603 filed on May 12, 2010, which claims the benefit of French Patent Application No. 0953147 filed on May 13, 2009. The entire contents of all of the above applications are hereby incorporated by reference.

The invention relates to an industrially effective method for preparing pharmaceutical formulations of paramagnetic metal ion chelates, and to the use of these formulations for preparing contrast agents for magnetic resonance imaging.

Numerous contrast agents based on lanthanide (paramagnetic metal) chelates, in particular gadolinium chelates, described for example in document U.S. Pat. No. 4,647,447, are known. Several products are sold, in particular macrocyclic chelates, such as DOTA (1,4,7,10-tetraazacyclododecane-N,N',N'',N'''-tetraacetic acid) gadoterate and gadoteridol BPDO3A, and linear chelates such as DTPA (diethylenetriaminepentaacetic acid) and DTPA-BMA (gadodiamide).

In the body, lanthanide chelates are in a situation of chemical equilibrium, which may lead to a risk of undesired release of lanthanide, and more especially of gadolinium. Those skilled in the art are thus led to seek solutions that limit this risk in order to solve the complex problem of tolerance in the patient completely safely. This problem is all the more difficult since the administration of contrast agents is often repeated during diagnostic examinations and/or for guiding and monitoring the efficacy of a therapeutic treatment.

Several approaches for improving the tolerance of gadolinium chelates are described in the prior art. More than twenty years ago, in particular through document U.S. Pat. No. 5,876,695, those skilled in the art worked on formulations comprising an excess of chelate in addition to the lanthanide-complexing chelate. This excess is intended to compensate for an undesired release of the lanthanide, the excess chelate then complexing with the released lanthanide (Gd3+ metal ion). Document U.S. Pat. No. 5,876,695 describes in particular an excess of linear chelate, in particular of free DTPA. Documents EP 450 078, U.S. Pat. No. 5,876,695 and US 2004/0170566 in particular describe the use of excipients written in the form X[X',L] where X' is a metal (in particular calcium) cation complexed by the chelate, and X is a metal cation used to obtain an uncharged salt of the complex [X',L] (negatively charged otherwise). X and X' are typically chosen independently of one another from sodium, zinc, magnesium and calcium ions, L representing the chelate. This excipient therefore makes it possible to add excess chelate.

Despite all these prior art studies, the complex problem of tolerance still exists, especially in situations with a more pronounced tolerance risk for the administration of MRI contrast products. A new problem has, moreover, recently appeared in terms of tolerance, namely a pathological condition known as NSF (nephrologic systemic fibrosis, or fibrogenic dermopathy), which might be correlated at least partly with the existence of gadolinium in the body. This disease has led to health authorities being alerted with respect to marketed gadolinium-based contrast agents for certain categories of patients.

In fact, this problem of tolerance of lanthanide chelates remains complex and considerable.

The applicant has shown, in the pending application FR0851055, the importance of and the difficulty in obtaining, on the industrial scale, for macrocyclic chelates, and in particular DOTA, formulations comprising an excess of free chelate and in a narrow and precise concentration range [0.002 to 0.4%] mol/mol, and in particular 0.025 to 0.25%. The term "free chelate" refers to a chelate not complexed by a lanthanide or a metal cation, therefore, contrary to the prior art, not in the form of an excipient of formula X[X',L] with X, X' and L as defined above. In order to solve this problem, the applicant has succeeded in developing a method for preparing a formulation of macrocyclic chelate, preferably DOTA, DO3A, HPDO3A or PCTA, more preferably DOTA, said method comprising at least one step of adjusting the amounts between the chelate and the lanthanide so as to obtain, in the final pharmaceutical solution (typically liquid injected into the patient), a mol/mol excess of chelate between 0.002 and 0.4%, and more especially between 0.02 and 0.3%, very advantageously between 0.025 and 0.25%.

The method described in this document advantageously comprises the following steps:

1) mixing the chelate and the lanthanide so as to obtain complexation of the lanthanide by the macrocyclic chelate, typically under hot conditions (advantageously between 60 and 90° C., preferably around 80° C.);
2) measuring the amounts of free chelate and/or of lanthanide in the solution obtained in step 1);
3) adjusting the amounts of chelate and/or of lanthanide.

Steps 2 and 3 are performed by any suitable means after having carried out the complexation.

Typically, an amount of chelate or of lanthanide is added so as to achieve the target concentration of free entities, typically of free DOTA. At the end of step 3), an adjusted pharmaceutical solution typically in liquid form, comprising the complex, in particular DOTA-Gd, and an excess of free chelate, in particular free DOTA (0.1 to 0.2%, for example), is thus obtained.

At the end of step 3, either this adjusted formulation in liquid form is the solution injected into the patient (where appropriate after addition of pharmaceutical excipients to this solution), or this adjusted formulation in liquid form is converted (typically by evaporation, freeze-drying, concentration or spray-drying) into a powder which may be returned to solution (where appropriate with addition of pharmaceutical excipients to this solution) to be injected into the patient.

It is recalled that many embodiment variants are included in the scope of the pending application FR0851055.

According to one of these variants, the excipient of the final formulation administered to the patient is added to the adjusted pharmaceutical solution obtained after complexation (step 1) above), this excipient being advantageously meglumine for DOTA-Gd. The liquid adjusted pharmaceutical solution thus obtained is ready to be administered to the patient. For DOTA for example, the solution administered contains the DOTA-Gd complex and a slight excess of free DOTA.

According to another variant, this pharmaceutical solution obtained after complexation is converted into a powder, so as to obtain this adjusted formulation in the form of a powder. For DOTA for example, this powder contains the DOTA-Gd complex and the slight excess of free DOTA targeted. If the formulation excipient (meglumine, for example) was introduced from the beginning of or shortly after the complexation, and before the conversion into powder, a powder which contains the complex and the excipient is obtained. The meglumine salt of gadoteric acid DOTA-Gd is thus obtained as a powder, this powder containing DOTA-Gd and free DOTA in excess in the targeted value range.

According to another variant, the adjusted pharmaceutical solution resulting from the complexation is converted into a material of powder type, by any suitable method, this powder subsequently being returned to solution with, firstly, an optional further adjustment by adding free DOTA to this solution for example and secondly, an addition of the formulation excipient, this excipient being advantageously meglumine for DOTA-Gd. A final liquid solution ready to be administered to the patient is obtained.

Among the industrial methods for preparing a powder, the applicant has now studied more closely the method of adjustment in the case of precipitation. Indeed, the method by precipitation in a solvent or a mixture of solvents is advantageous for an industrial production.

Those skilled in the art deduce directly from the text and the examples of FR0851055 that the solution obtained at the end of step 1) or at the end of step 3) can be precipitated, from a suitable organic solvent, so as to obtain a powder which may itself be returned to solution, this solution being injected into the patient. As described in the pending application FR0851055, the proportions, in the powder, of DOTA-Gd and of free DOTA are typically the same between, on the one hand, the adjusted solution and, on the other hand, the powder.

It so happens that, by carrying out tests, the applicant has now noted that the precipitation poses an additional problem of optimization on the industrial batch scale, given the amounts and the solvents used. More specifically, the applicant has noticed that the conversion, by precipitation, of the liquid solution S obtained in step 1 or at the end of step 3), of the method described in FR0851055, into a powder P is typically accompanied by a modification of proportions of the entities, between, on the one hand, this pharmaceutical solution S and, on the other hand, the powder P, with regard to the following entities:
  i) the complexed chelate (DOTA-Gd complex, for example),
  ii) the free chelate (free DOTA, for example) as defined above.

In order to control the method by precipitation, and in particular to be sure that the pharmaceutical formulation solution to be administered contains the target excess amount of free chelate (free DOTA in particular, from 0.002% to 0.4%), the applicant has developed a method for preparing a pharmaceutical formulation of lanthanide chelate (advantageously of macrocyclic chelate of lanthanide) (with or without pharmaceutical excipient such as meglumine) in power form, this powder comprising a mol/mol excess of free chelate of between 0.002 and 0.4%, said method comprising the following successive steps:
  1) step 1: mixing the chelate (advantageously the macrocyclic chelate) and the lanthanide so as to obtain complexation of the lanthanide by the chelate, the complexation solution obtained comprising, in addition to the chelate-lanthanide complex, an excess amount X1 of free chelate;
  2) step 2: preferably measuring X1, and optionally adjusting X1 so as to have X1 between 0.002 and 0.4% mol/mol;
  3) step 3: precipitating the complexation solution obtained in step 1) from an organic solvent so as to obtain a powder of chelate-lanthanide complex, the powder containing an excess amount X2 of free chelate,
  4) step 4: optionally adjusting X2 so as to obtain:
    4.a) X2 is between 0.002 and 0.4% mol/mol, and more especially between 0.02 and 0.3% mol/mol, very advantageously between 0.025 and 0.25% mol/mol, and
    4.b) X2 corresponds to between 0.1 and 5 times X1, advantageously between 0.2 and 2 times X1, in particular between 0.5 and 1.5 times X1;
  5) step 5: preferably measuring X2.

For the purpose of the present invention, the term "free chelate" is intended to mean any chelate not complexed with a lanthanide or a metal cation, therefore, contrary to the prior art, not in the form of an excipient of formula X[X',L] with X, X' and L as defined above.

Step 4) of adjusting X2 can be carried out by adding or removing free chelate by any suitable means (resin, for example), or by adding or removing lanthanide.

Advantageously, X2 belongs to the Ranges:
  1) [0.1–0.95]×X1 (X2 corresponds to between 0.1 and 0.95 times X1), even more advantageously [0.2–0.95]×X1, particularly [0.5–0.95]×X1, more particularly [0.6–0.9]×X1, or
  2) [1.05–5]×X1 (X2 corresponds to between 1.05 and 5 times X1), even more advantageously [1.05–2]×X1, in particular [1.05–1.5]×X1, even more particularly [1.05–1.3]×X1.

According to embodiments, the solvent of step 3) is chosen from: ethanol, methanol, propanol, isopropanol, methyl ethyl acetone, ethyl acetate, and mixtures thereof (including water/solvent in any proportions) known to those skilled in the art, advantageously ethanol, methanol and propanol.

According to embodiments, the solvent of step 3) is used according to a ratio of from 5 to 20 volumes of solvent per volume of complexation solution, advantageously 10 to 20 volumes of solvent per volume of complexation solution.

According to embodiments, the solvent of step 3) is used at a temperature included in the range [0-80° C.], in particular between 30 and 70° C.

According to embodiments, a partial concentration of the complexation solution is performed (for example by evaporation), before carrying out step 3) of precipitating from the solvent.

According to embodiments, the pH of the complexation solution used in step 3) is between 1 and 9.

Advantageously, the following conditions will be used during step 3):
  pH: [2-8]
  [ethanol solvent]: 10 to 20 volumes per volume of complexation solution Temperature: [0; 50]° C.

Advantageously, the powder obtained in step 3) or in step 4) is returned to solution so as to form a pharmaceutical composition in liquid form.

Step 1 preferably uses an excess chelate, advantageously of DOTA, relative to the stoichiometric proportions, so as to obtain an amount X1 of free chelate, advantageously of free DOTA.

Step 1 can be carried out in a single step or optionally in several successive steps by measuring and adjusting so as to have an amount X1 of free chelate, advantageously of free DOTA (preferably between 0.002 and 0.4% mol/mol). For example, step 1) comprises the following successive substeps:

1.1. complexation in solution
1.2. measuring the chelate, advantageously the DOTA, and/or the lanthanide that is free (advantageously Gd)
1.3. adding chelate, advantageously DOTA, so as to complex the possible free lanthanide (if there is any at the end of step 1) and to obtain an amount X1 of free chelate, advantageously of free DOTA (preferably between 0.002 and 0.4% mol/mol).

For the purpose of the present invention, the term "free lanthanide" is intended to mean any lanthanide that is not complexed and in particular not complexed by the chelate.

This variant with step 1.1 to 1.3 is advantageous since the isolation of a powder makes it possible to be able to purify the product.

Advantageously, the lanthanide complex is the DOTA-Gd complex.

Thus, the controlling of the precipitation step coupled with the prior measuring of the amount X1 of free chelate, advantageously free DOTA, provides an adjustment of the level of chelate, advantageously of DOTA, making it possible to solve the problems addressed by the invention.

Typically, the detailed measurements will be carried out for each industrial production batch. It will also be possible, provided that the characterization of the products used is completely controlled, to construct a calibration reference matrix obtained by virtue of the measuring and adjusting step(s) described in the application.

It is clear for those skilled in the art that optimization substeps can be inserted between these main steps.

The precipitation in step 3) can be carried out by adding the solvent to the complexation solution, or conversely by adding the complexation solution to the solvent.

Advantageously, the powder obtained after precipitation (step 3) is subsequently returned to solution, firstly, with or without optional further adjustment by adding free chelate (DOTA, for example) to this solution, and secondly, with an optional addition of formulation excipient, this excipient being advantageously meglumine for DOTA-Gd. A final liquid solution ready to be administered to the patient is obtained. If meglumine has been introduced into the complexation solution at the start, the powder will comprise DOTA-Gd, excess free DOTA, and meglumine.

According to one embodiment, the solution of step 1 does not comprise the positive counterion (typically meglumine or the $Na^+$ ion). Step 3 will thus consist in precipitating not DOTA-Gd in salt, typically sodium salt, or meglumine form (more specifically, $[DOTA]Gd^-,Na^+$ or $[DOTA-Gd]^-$, $CH_2OH-(CHOH)_4-CH_2-N^+-CH_3$), but its protonated form $[DOTA-Gd]^-,H^+$, this step being carried out in an acidic medium.

According to another embodiment, which is moreover advantageous and not described in the prior art, the solution of step 1 comprises the positive counterion (meglumine in particular); step 3 thus consists in precipitating, according to suitable conditions (in particular of pH and of amount of solvent), the DOTA-Gd meglumine salt $[[DOTA-Gd]^-$, $CH_2OH-(CHOH)_4-CH_2-N^+-CH_3]$. For this, 10 to 20 volumes, for example 10 to 15 volumes, of ethanol or methanol solvent, per complexation volume, are for example used, advantageously at a pH between 5 and 8 and a temperature of 25-60° C. This makes it possible to use a DOTA-Gd complex in salt form, which is more stable than the protonated form (owing to the complexation constants).

To this effect, the invention also relates to a method as described above in the application, the complexation solution of step 1 being a solution of DOTA-Gd meglumine salt or sodium salt, the [DOTA-Gd] complex not being in its protonated form in this solution. Very preferably, the complexation solution of step 1 is a solution of [DOTA-Gd] meglumine salt, which has the advantage, compared with a solution of DOTA-Gd sodium salt, when a meglumine formulation that is advantageous for the patient from the tolerance point of view is prepared, of not having to subsequently replace the sodium with meglumine, this being an operation that is industrially complex.

The invention also relates to the use of a powder obtained by means of the method of the applicant, for preparing a liquid pharmaceutical formulation comprising a mol/mol excess of free chelate of between 0.002 and 0.4%.

The invention also relates to a method for preparing a liquid pharmaceutical formulation comprising a mol/mol excess of free chelate of between 0.002 and 0.4%, said method comprising the following successive steps:
  a) obtaining a powder according to the precipitation method of the present invention,
  b) putting the powder obtained in step a) into solution, with, where appropriate, the addition of at least one formulation excipient and, where appropriate, the addition of additional free chelate.

Moreover, it is specified that the method by precipitation of the present application includes the method described, and optional variants (particular variants of crystallization methods, for example) which are reflected by a modification of the proportions of the complexed-chelate and free-chelate entities between, on the one hand, the pharmaceutical composition in liquid solution form and, on the other hand, the pharmaceutical composition in powder form.

Detailed examples are now described, illustrating the method for preparing lanthanide chelate formulations with a precipitation step, and more particularly the preparation by precipitation of formulations comprising an excess chelate for DOTA.

The following table indicates an example of the amounts used for producing a solution of 100 liters of DOTA (industrial amount).

| Component | Amount |
| --- | --- |
| DOTA (1) | 20.100 kg (i.e. 0.497M) |
| Gadolinium oxide (expressed as anhydrous product) $Gd_2O_3$ | 9.135 kg (i.e. 0.252M) |
| Meglumine (expressed as anhydrous product) | 9.215 kg |
| Solution for adjustment of DOTA at 15% (w/v) | 15-35 mg per 100 ml |
| qs level of free DOTA | |
| Solution of meglumine at 2N qs pH = 6.8-7.4 at 20° C. | |
| Injectable water . . . qs | 100 liters |

(1) 1,4,7,10-tetraazacyclododecane-N,N',N'',N'''-tetraacetic acid

Step 1.1: Complexation in Solution

The DOTA and the gadolinium oxide are dispersed in injectable water at approximately 80° C. The gadolinium oxide in the presence of DOTA forms a complex-acid that is soluble in water.

40 liters of injectable water at 80° C. are placed in a 100 liter production tank, the injection of nitrogen is started, and then the 20.100 kg of DOTA and the 9.135 kg of gadolinium oxide are incorporated with stirring. The complexation is carried out at a pH below 6.

Steps 1.2. and 1.3.: Adjustment of the Free Entities

The adjustment of the solution is advantageously carried out with gadolinium oxide or DOTA.

At the end of step 1.1, the following steps are carried out:
1.2. taking a sample and assaying the free gadolinium,
1.3. adding a solution for adjustment of DOTA, quantity sufficient for an amount of
15-35 mg per 100 ml.

A complexation solution S with a level X1 of free chelate that can be measured (step 2) is obtained. It is also possible to remove any residual gadolinium by virtue of a chelex resin for example prerinsed with water (a quantification of the free gadolinium can be carried out by means of a colorimetric assay with Arsenazo (III) before this removal, and optionally also afterwards). For this, the reaction mixture can be brought back to pH 5 (the resin is more effective). The whole mixture is left to stir at ambient temperature for 2 hours. The pH rises again to between 6.5 and 7. The resin is removed by filtration.

The value X1 (as a percentage mol/mol) is, according to batches, for example between 0.005 and 0.1%, in particular 0.01 and 0.05% mol/mol of free DOTA (DOTA not complexed by Gd, nor by cations such as $Ca^{2+}$).

Step 3: Precipitation of the Complexation Solution

The solution obtained in step 2 can be directly added to the solvent, but, in order to reduce the amounts of solution to be treated, a prior concentration under vacuum is typically carried out without significant modification of the level of free DOTA.

The aqueous solution of DOTA-Gd is concentrated under vacuum at a temperature below 80° C. (for example between 20 and 60° C., for example 50 to 70° C.) to a concentration of 0.5 kg (+/−0.2 kg) per kg of solution. The solution is cooled to ambient temperature. For an amount of 1 kg of concentrated solution, a solution of 5 to 20 liters (preferably 10 to 20 liters, and typically 20 liters) of ethanol is added to 1 kg of concentrated solution. The precipitated DOTA-Gd obtained is filtered off, and then taken up with 3-4 liters of ethanol.

Related back to an industrial amount of 100 kg of DOTA-Gd solution, an amount of about 2000 liters of ethanol will thus, for example, be used to carry out the precipitation. The product obtained is dried under vacuum at a temperature below 80° C.

The following denatured ethanol is, for example, used: 95% ethanol, 5% mixture of ethyl acetate and isopropanol.

The compound obtained by precipitation (powder) contains an amount X2 of free chelate. According to the solvents used, an amount X2 (as a percentage mol/mol) which varies according to the tests, for example, between 0.02% and 0.15% mol/mol, is obtained.

Moreover, the results are not always identical depending on whether the precipitation is carried out from a solution of DOTA-Gd (with excess X1 of free DOTA) with meglumine, or from a solution of DOTA-Gd (with excess X1 of free DOTA) without meglumine, wherein the meglumine is to be taken into account from the point of view of the solubilization.

Step 2a Optional after Step 2 and Before Step 3: Cooling

The final solution of step 2 is cooled to 30° C., for example by circulation of cold water in the jacket of the tank.

Step 2b Optional after Step 2a and Before Step 3: Adjustment of the pH and of the Density The acid function of the complex formed is salified with meglumine and the pH at 20° C. is adjusted to 6.8-7.4. The concentration is adjusted by adding injectable water.

The following are placed in the production tank:
9.125 kg of meglumine
and a solution of meglumine at pH=7.3-7.4 at 2 N and qs injectable water.

Step 5 after Step 3 or 4:

The precipitated product in powder form obtained is returned to a pharmaceutical aqueous solution (typically comprising meglumine), subsequently filtered, and then placed in vials that are typically sterilized by autoclaving.

What is claimed is:

1. A method for preparing a pharmaceutical formulation of a macrocyclic chelate of a lanthanide, said macrocyclic chelate being DOTA, said lanthanide being Gadolinium, said macrocyclic chelate of a lanthanide being DOTA-Gd complex, and said method comprising the following successive steps of:
    (1) mixing in a solution a macrocyclic chelate and a lanthanide so as to obtain a complexation solution of the lanthanide by the macrocyclic chelate, the complexation solution comprising, in addition to the macrocyclic chelate-lanthanide complex, an excess amount X1 of free macrocyclic chelate, wherein a step (1) is carried out in a single step or in several successive steps by measuring and adjusting, so as to have an amount X1 of free macrocyclic chelate, and the step (1) comprises the following successive substeps of:
        (1.1) complexing in solution the lanthanide with the macrocyclic chelate,
        (1.2) measuring the macrocyclic chelate and/or the lanthanide that is free, and
        (1.3) adding free macrocyclic chelate, so as to complex the free lanthanide if any remains at the end of step (1.1), and to obtain an amount X1 of free macrocyclic chelate;
    (2) optionally measuring X1 and/or adjusting X1 so as to have X1 between 0.002 and 0.4% mol/mol;
    (3) precipitating or crystallizing the complexation solution obtained in step (1) from an organic solvent, so as to obtain a powder of the macrocyclic chelate-lanthanide complex, said powder containing an excess amount X2 of free macrocyclic chelate, wherein X2 represents the amount of free macrocyclic chelate obtained after precipitation or crystallization and X2 is less than X1;
    (4) adjusting X2 by adding or removing free macrocyclic chelate or by adding or removing lanthanide so as to obtain:
        (4.a) X2 between 0.002 and 0.4% mol/mol, and
        (4.b) X2 corresponding to between 0.2 and 5 times X1, wherein said powder obtained after step (4) comprises a mol/mol excess of free macrocyclic chelate of between 0.002 and 0.4%; and
    (5) returning said powder to solution so as to form a pharmaceutical composition in liquid form, said pharmaceutical composition in liquid form being ready for administration to a patient.

2. The method of claim 1, wherein, in step 3), the precipitating or crystallizing of the complexation solution obtained in step (1) is carried out at a pH in the range 1 to 9.

3. The method of claim 1, wherein the solvent of step (3) is chosen from ethanol, methanol and propanol.

4. The method of claim 1, wherein the solvent of step 3) is used according to a ratio of from 10 to 20 volumes of solvent per volume of complexation solution.

5. The method of claim 1, wherein the solvent of step 3) is used at a temperature included in the range of 0° C. to 80° C.

6. The method of claim 1, wherein the complexation solution of step (1) is a solution of [DOTA-Gd], further comprising a meglumine salt.

7. The method of claim 1, wherein in step (4), X2 is adjusted so as to be comprised between 0.02 and 0.3% mol/mol.

8. The method of claim 1, wherein in step (4), X2 is adjusted so as to be comprised between 0.025 and 0.25% mol/mol.

9. The method of claim 1, wherein in step (4), X2 is adjusted so as to belong to the range: [0.5-0.95]×X1.

10. The method of claim 5, wherein the temperature is included in the range of 30 to 70° C.

11. The method of claim 1, wherein any free gadolinium is removed by virtue of a chelex resin in the complexation solution S with a level X1 of free macrocyclic chelate obtained after step 1.3.

12. The method of claim 11, wherein a quantification of the free gadolinium is carried out by means of a colorimetric assay with 2,2'-(1,8-dihydroxy-3,6-disulfonaphthylene-2,7-bisazo)bisbenzenearsonic acid before and optionally also afterwards the removal of this free gadolinium.

13. The method of claim 11, wherein the said resin is removed by filtration.

* * * * *